United States Patent
Hung et al.

(10) Patent No.: US 7,676,274 B2
(45) Date of Patent: Mar. 9, 2010

(54) HIGH-DENSITY ARRAY OF MICRO-MACHINED ELECTRODES FOR NEURAL STIMULATION

(75) Inventors: Andy Hung, Irvine, CA (US); Robert Greenberg, Los Angeles, CA (US); Dau Min Zhou, Saugus, CA (US); Jack Judy, Los Angeles, CA (US); Neil Talbot, Montrose, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 828 days.

(21) Appl. No.: 10/160,468

(22) Filed: May 1, 2002

(65) Prior Publication Data

US 2003/0195601 A1   Oct. 16, 2003

Related U.S. Application Data

(60) Provisional application No. 60/287,415, filed on May 1, 2001, provisional application No. 60/314,828, filed on Aug. 24, 2001.

(51) Int. Cl.
    *A61N 1/00* (2006.01)
(52) U.S. Cl. .................................... 607/116
(58) Field of Classification Search ......... 607/116–141, 607/69; 600/373–381; 73/25.03; 333/186; 219/69.15; 606/48, 152
See application file for complete search history.

(56) References Cited

U.S. PATENT DOCUMENTS

| | | | |
|---|---|---|---|
| 4,240,878 A | 12/1980 | Carter | |
| 4,750,977 A | 6/1988 | Marrese | |
| 4,953,387 A * | 9/1990 | Johnson et al. | 73/25.03 |
| 4,969,468 A * | 11/1990 | Byers et al. | 600/373 |
| 5,109,844 A | 5/1992 | deJuan, Jr. et al. | |
| 5,215,088 A * | 6/1993 | Normann et al. | 600/377 |
| 5,286,944 A * | 2/1994 | Li | 219/69.15 |
| 5,357,073 A * | 10/1994 | Tominaga et al. | 219/69.15 |
| 5,531,774 A | 7/1996 | Schulman et al. | |
| 5,935,155 A | 8/1999 | Humayun et al. | |
| 5,944,717 A * | 8/1999 | Lee et al. | 606/48 |
| 6,171,239 B1 * | 1/2001 | Humphrey | 600/372 |
| 6,503,231 B1 * | 1/2003 | Prausnitz et al. | 604/272 |
| 6,628,177 B2 * | 9/2003 | Clark et al. | 333/186 |
| 6,676,675 B2 * | 1/2004 | Mallapragada et al. | 606/152 |
| 6,829,498 B2 * | 12/2004 | Kipke et al. | 600/378 |
| 2003/0208248 A1 * | 11/2003 | Carter et al. | 607/69 |

* cited by examiner

*Primary Examiner*—George Manuel
(74) *Attorney, Agent, or Firm*—Scott B. Dunbar

(57) ABSTRACT

The present invention is a micro-machined electrode for neural-electronic interfaces which can achieve a ten times lower impedance and higher charge injection limit for a given material and planar area.

36 Claims, 2 Drawing Sheets

HIGH-DENSITY ARRAY OF MICRO-MACHINED ELECTRODES FOR NEURAL STIMULATION

CROSS REFERENCE TO RELATED APPLICATIONS

This application claims benefit of provisional applications 60/287,415, filed May 1, 2001, entitled High-Density Arrays of Micro-machined Electrodes for Neural Stimulation Systems, and 60/314,828, filed Aug. 24, 2001, entitled Micro-machined Electrodes for High Density Neural Stimulation Systems.

GOVERNMENT RIGHTS

This invention was made with government support under grant No. R24EY12893-01, awarded by the National Institutes of Health. The government has certain rights in the invention.

FIELD OF THE INVENTION

This application relates to an improved electrode, in particular, and improved electrode for neural stimulation having an increased surface area.

BACKGROUND OF THE INVENTION

Micromachining has been used to produce neural-electronic interfaces for recording neural activity with cortical probe arrays and planar arrays to form individual cells and clusters of cells. Recently, however, new applications that require the stimulation of neural tissue push the performance limits of conventionally produced microelectrodes. One good example is the development of a visual prosthesis. Blind patients with retinits pigmentosa or macular degeneration (i.e., photoreceptors do not function) observe a visual percept induced by the direct electrical stimulation of the retina. Internationally, several efforts are under way to construct a fall visual prosthetic system.

Examples of implantable nerve stimulators that benefit from very small electrodes are U.S. Pat. No. 5,109,844 ("De Juan"), U.S. Pat. No. 5,935,155 ("Humayun"), and U.S. Pat. No. 5,531,774 ("Schulman"). De Juan and Humayun disclose systems for the electrical stimulation of the retina by a retinal electrode array held against the retina. DeJuan describes an epiretinal electrode array. Humuyan describes a system for capturing a video image, transferring the image wirelessly into a living body and applying the image to a retinal electrode array. Schulman discloses a cochlear stimulator for the deaf.

While small electrodes help create a precise signal to stimulate a single nerve or small group of nerves, the ability of an electrode to transfer current is proportional to its surface area. It is further known that electrical signals transfer more efficiently from an edge than from a flat surface. It is, therefore, desirable for an electrode to have a large surface area with many edges.

One technological challenge is the trade off between electrode density and stimulation current. Although the total charge injection required to illicit a visual percept is generally believed to be fixed, the current used is limited by the electrode area when operated at the maximum current density before undesirable and irreversible electrochemical reactions occur. The result is that the electrode size and density in existing retinal prosthetic development efforts are limited.

Therefore, it is advantageous to increase the total surface area of an electrode without increasing the planar surface area. This can only be accomplished by increasing the vertical surface area. One method of increasing surface area is to roughen the surface by rapid electroplating. This is commonly done with platinum electrodes and known as platinum black as described in U.S. Pat. No. 4,240,878 ("Carter"). Platinum black is not very strong and tends to flake off. This is unacceptable in a neural stimulator. The flaking can be limited by ultrasonic vibrations as described in U.S. Pat. No. 4,750,977 ("Marrese"), but not eliminated. A system is needed to create a high surface area electrode which is strong enough for human implantation.

SUMMARY OF THE INVENTION

The present invention is a micro-machined electrode for neural-electronic interfaces which can achieve a ten times lower impedance and higher charge injection limit for a given material and planar area. By micro machining posts or other protuberances on the surface of an electrode, the surface area of the electrode is increased, thus improving the electrical characteristics of the electrode.

BRIEF DESCRIPTION OF THE DRAWINGS

Preferred embodiments demonstrating the various objectives and features of the invention will now be described in conjunction with the following drawings.

DETAILED DESCRIPTION OF THE PREFERRED EMBODIMENTS OF THE INVENTION

Figure 1:
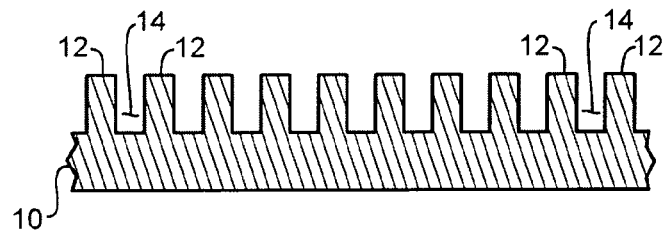
FIG. 1 shows an electrode according to the present invention.

Referring to FIG. 1, the present invention is an electrode with a high aspect ratio surface plated or cut to create maximum surface area within a given planar surface area. The electrode includes a planar base 10, covered with micromachined posts 12 and valleys 14. Alternatively, ridges can be micromachined to increase strength. By making the ridges curved in the horizontal direction strength is increased. While one of skill in the art may think of many possible shapes, any micromachined protuberances are believed to fall within the spirit of the invention. Micromachining techniques can create posts with an aspect ratio of 2 or more. That is, posts which are twice as high as they are wide. Since the area of a surface covered in posts is equal to the horizontal area plus one times the height divided by the width, an increase of surface are by a factor of three is easily obtainable.

Figure 2:
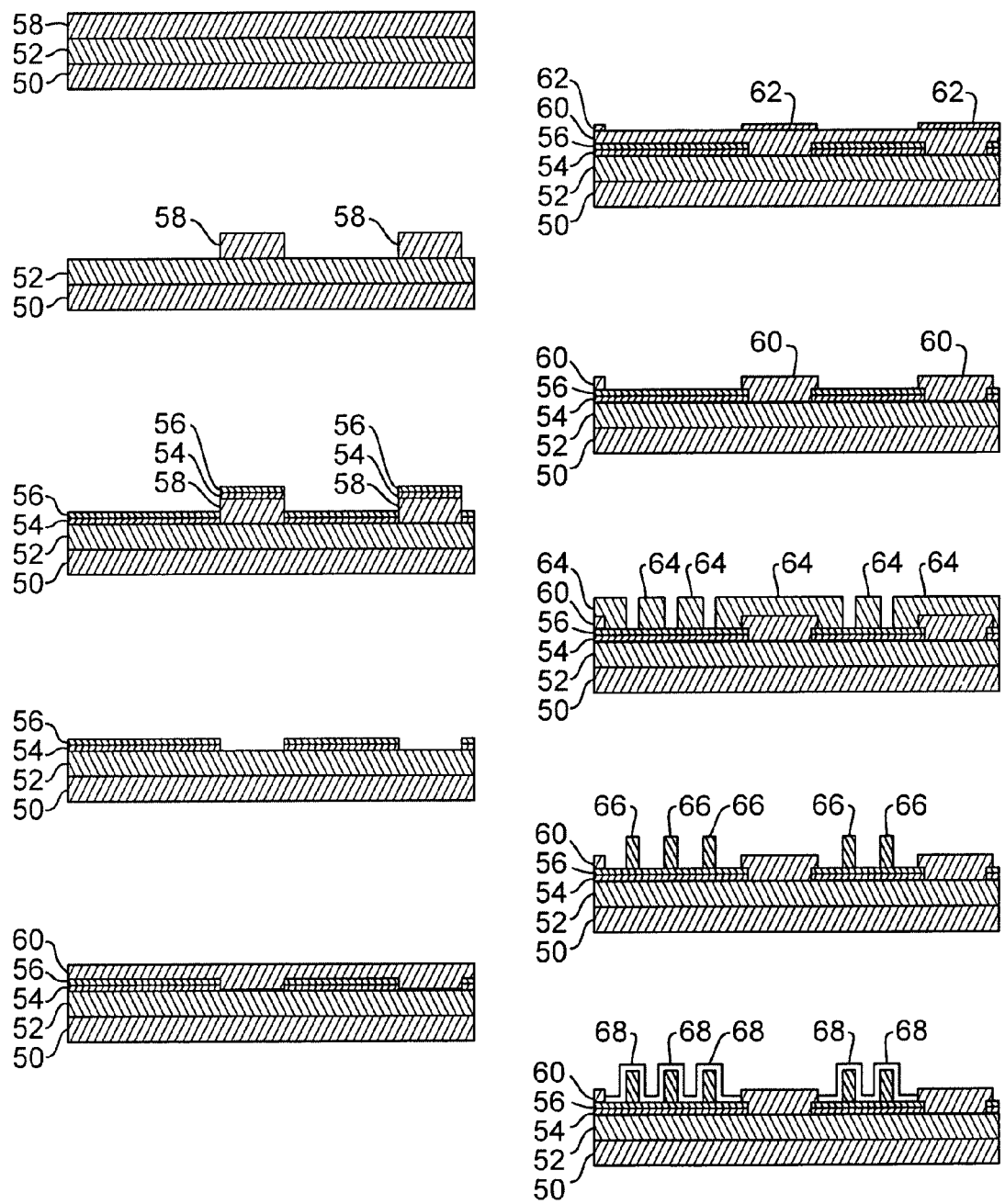
FIG. 2 shows the steps of forming an electrode array according to present invention.

Referring to FIG. 2, the present electrode is formed by techniques similar to that of manufacturing semiconductors. A photoresist layer is applied by photolithographic techniques. Then, an etching acid is used to remove material not protected by the photoresist layer, or material is plated to metals not protected by the photoresist. Electrode arrays according to the present invention can be formed on flexible or rigid substrates. The preferred embodiment is built on a polyimide flexible substrate using titanium and platinum, gold or a combination of platinum and gold. Polyimide is used as a supporting material and for electrical isolation. The fabrication process begins with a silicon wafer, 50, which simply acts as a passive substrate, which is later removed A 5 μm lower polyimide film 52 is deposited to form the lower insulator and base to supply mechanical support for the flexible array. For a rigid substrate, the lower polyimide film 52 may be replaced by silicon dioxide, aluminum oxide, silicon carbide, diamond, or zirconium oxide film, and the silicon wafer 50 is not removed. The electronic base of the electrode array and the interconnect is formed by a 100 nm film of titanium 54, followed by a 100 nm film of platinum 56 deposited by electron-beam evaporation. Titanium adheres better to polyimide than platinum and is provided under the platinum for adhesion purposes. Prior to depositing the metal films 54 and 56 to the polyimide a photoresist layer 58 is patterned on the lower polyimide film 52. A lift-off process that uses STR 1045 photoresist 58 and an acetone soak are used to pattern the metal films 54 and 56. An upper polyimide film 60 is spun on to a thickness of 5 μm and then hard baked at 350° C. to form a structure in which the titanium film 54 and platinum film 56 is sandwiched between two insulating polyimide layers 52 and 60.

The upper polyimide film 60 must be patterned to expose the electrode sites. To accomplish this we first deposit and pattern an aluminum etch mask 62 and then remove all unprotected polyimide in an oxygen/$CF_4$ gas mix plasma etch.

A 25 μm layer of photoresist 64 is used to define openings for the subsequent electroplating of the high aspect ratio microstructures made of platinum or gold. Platinum or gold posts 66 are plated on to the platinum film 56. If the thickness of the plated platinum posts 66 exceeds 0.5 μm, the high stress in the platinum posts 66 may cause the platinum posts 66 to delaminate from the platinum film 56 or lift up the platinum film 56 from the lower polyimide film 52. Gold structures exhibit better plating characteristics but are less stable under electrical stimulation. Therefore, it is advantageous to plate micro post 66 first with gold and then a with platinum layer 68 over the top of the gold microposts 66.

New platinum plating technologies show promise for overcoming platinum plating problems. If so, it may be useful to first plate platinum posts covered with Iridium or Iridium oxide. Iridium has electrochemical advantages and is even more difficult to plate than platinum. Other materials may also make an effective final layer and may be plated over platinum or gold, these include titanium oxide, rhodium palladium.

If gold is used in microposts 66, it is important that the layer over the gold 68 be hermetic. While the preferred embodiment uses electroplating, other methods are known in the art for making thin hermetic layers such a sputtering, ion-beam deposition, and ion-beam assisted deposition. This methods can also be used for depositing the metal films 54 and 56 on the polyimide film 52. In addition to plating, the microposts 66 may be micromachined by etching or lift off techniques. Once the high aspect ratio structures have been plated, the photoresist plating mask is removed and the electrodes are electrochemically tested. In the final step, the silicon base 50 is removed.

Initially the electrode surfaces consisted of arrays of microposts or the inverse, micromesh. However, due to the stress in the electrodeposits, the much larger structures formed for the mesh electrode geometry was found to be impractical for platinum.

It is possible to cause electrodeposition to occur on the sidewalls of the photoresist plating mold. This yields hollow micropost and further increases the surface area. During the normal developing process, the KOH-based developer removes the exposed regions of the photoresist and then is rinsed away thoroughly. If the rinsing procedure is inadequate, the KOH-based developer is not efficiently diluted, particularly from the sidewalls. Conductivity is high enough to act as a seed layer during electrodeposition. In fact, a cross section of a hollow cylindrical micropost reveals that indeed the thickness of the plated material on the base of the hollow micropost is the same as that grown on the sidewalls of the exposed photoresist. It is also noteworthy that only the sidewalls of the resist become plated and not the top surface of the photoresist. A systematic study of the impact of the rinsing process on sidewall plating showed that when a developed sample is soaked in stagnant water for less than 10 minutes, plating will occur on the photoresist side walls. Longer soaks result in the expected results (i.e., flat plating of the electrode surface up through the plating mold to result in a solid micropost). The sidewall plating process has been found to be reproducible also for the electrodeposition of platinum, gold, and even nickel.

Figure 3:
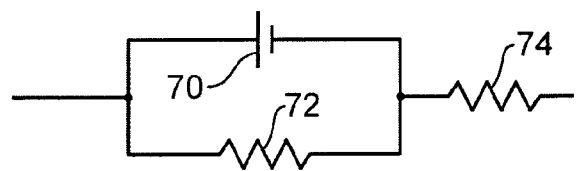
FIG. 3 shows the electrical circuit equivalent of a neural stimulation electrode.
Figure 4:
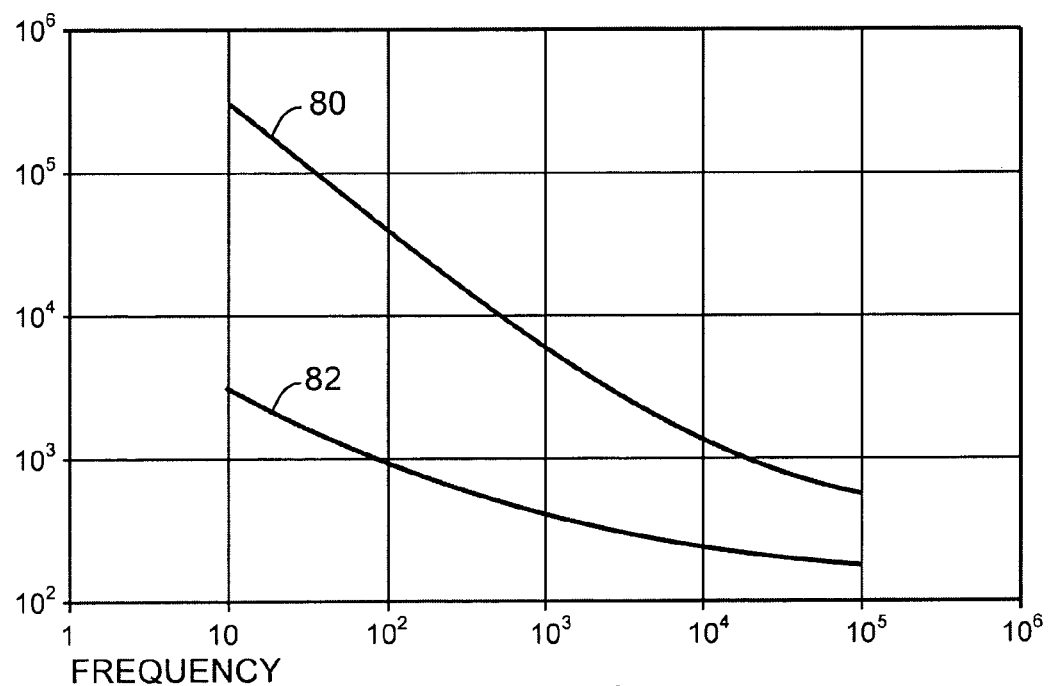
FIG. 4 shows applicant's test results from use of the preferred electrode.

To characterize the electrochemical dependence of electrode area for the flat and micromachined structures an impedance analyzer was used to measure the current induced by the application of a small voltage fluctuation (e.g., 5 mV) as show in FIG. 4. Typically an electrode surface can be modeled (as shown in FIG. 3) with a capacitance 70 and resistance 72 in parallel and a solution resistance 74 in series. The capacitance 70 of the electrode corresponds to the fast charge build up across the electrode electrolyte interface when voltage is applied. The electrode-electrolyte resistance 72 describes the lower faradic conductance of charge transfer by means of chemical reaction between solution and the electrode metal. The solution resistance 74 represents the resistance of the solution.

The capacitance 70 and resistance 72 values typically vary widely with voltage, time, and concentration, and are challenging to model precisely. However, because our experiment setup employs small alternating voltage fluctuations, resistance 70, capacitance 72 and solution resistance 74, can be approximated by simple linear values over the small voltage range. Since capacitance 70 is proportional to surface area and resistance 72 is inversely dependent on area, the resulting parallel conductance is also directly proportional to surface area.

Thus proportionality between conductance and surface area is observed in our experimental impedance measurements. From the impedance curve of each electrode sample (FIG. 4) the value is taken at 1 kHz and plotted against the estimated surface area. A flat electrode curve 80 shows the impedance of a flat electrode at various frequencies. A micromachined electrode curve 82 shows lower impedance for the micromachined electrode, with a greater improvement at lower frequencies. For structures with an aspect ratio of height divided by width equal to 1, doubling of the effective electrode impedance is expected and observed. However, when the aspect ratio is increased further to realize a larger surface area, experimental results show that improvement in conductance advantage plateaus at a 4× increase in physical surface area. Since the plateau can be overcome to obtain larger increases in conductance with surface area, the measured conductance is limited by the solution resistance 74 in the high-aspect ratio features.

The above detailed description is provided to illustrate the specific embodiments of the present invention and is not intended to be limiting. Numerous variations and modifications are possible within the scope of the present invention. The present invention is defined by the following claims.

We claim:

1. An electrode suitable to stimulate neural tissue having an electrode physical surface area, the electrode comprising:
   a conductive electrode base having a base surface area;
   a plurality of micromachined protuberances on said electrode base, each protuberance having a height and a width; and
   a conductive layer covering said plurality of conductive micromachined protuberances, wherein said conductive layer provides enhanced stability to the electrode under electrical stimulation;
   wherein the plurality of conductive micromachined protuberances have an aspect ratio of height divided by width equal to or higher than 1 and the electrode physical surface area is at least 4 times the base surface area; and
   wherein said physical surface area results in at least two orders of magnitude reduction in the electrode impedance at low frequencies relative to said base surface area.

2. The electrode according to claim 1, wherein said protuberances are posts.

3. The electrode according to claim 2, wherein said post are hollow posts.

4. The electrode according to claim 1, wherein said protuberances are ridges.

5. The electrode according to claim 1, wherein said protuberances comprise platinum.

6. The electrode according to claim 1, wherein said protuberances comprise gold.

7. The electrode according to claim 1, wherein said protuberances comprise gold and said conductive layer is made of platinum.

8. The electrode according to claim 1, wherein said protuberances comprise iridium.

9. The electrode according to claim 1, wherein said protuberances comprises iridium oxide.

10. The electrode according to claim 1, wherein said protuberances comprise titanium oxide.

11. The electrode according to claim 1, wherein said conductive layer forms a hermetic seal over said protuberances.

12. An electrode array suitable to stimulate neural tissue having an electrode physical surface area, the electrode array comprising:
    a lower flexible insulating layer; a flexible conductive layer;
    a flexible conductive layer having a conductive layer surface area;
    an upper flexible insulating layer including voids exposing portions of said flexible conductive layer; and
    conductive micromachined protuberances on said portions of said flexible conductive layer, each of said conductive machined protuberances having a height and width, each of said conductive micromachined protuberances covered by an upper conductive layer;
    wherein the plurality of micromachined protuberances have an aspect ratio of height divided by width equal to or higher than 1, and the physical electrode surface is at least 4 times the conductive layer surface area;
    wherein said conductive layer provides enhanced stability to the electrode under electrical stimulation; and
    wherein said physical surface area results in at least two orders of magnitude reduction in the electrode impedance at low frequencies relative to said conductive layer surface area.

13. The electrode array according to claim 12, wherein at least one of said flexible insulating layers comprising polyimide.

14. The electrode array according to claim 12, wherein said flexible conductive layer comprises platinum.

15. The electrode array according to claim 12, wherein said flexible layer comprises titanium.

16. The electrode array according to claim 12, wherein said protuberances comprise gold.

17. The electrode array according to claim 12, wherein said protuberances are posts.

18. The electrode array according to claim 17, wherein said post are hollow posts.

19. The electrode array according to claim 12, wherein said protuberances are ridges.

20. The electrode array of claim 12, wherein said upper conductive layer comprises a material selected from the group consisting of platinum, rhodium, palladium, iridium, iridium oxide and titanium oxide.

21. A method of increasing an electrode effective surface area comprising:
    providing an electrode base having a base surface area;
    micromachining conductive protuberances on the base surface area, each of said protuberances having a height and a width; and
    depositing a conductive material on said conductive protuberances to form an upper conductive layer;
    wherein the conductive protuberances have an aspect ratio of height divided by width equal to or higher than 1 and the electrode effective surface area is at least 4 times the base surface area;
    wherein said conductive layer provides enhanced stability to the electrode under electrical stimulation; and
    wherein said physical surface area results in at least two orders of magnitude reduction in the electrode impedance at low frequencies relative to said base surface area.

22. The method of claim 21, wherein said protuberances are micromachined from platinum.

23. The method of claim 21, further comprising the step of depositing said electrode base on an insulating later.

24. The method of claim 23, wherein said insulating layer is polyimide.

25. The method according to claim 21, further comprising the steps of:
    depositing an upper insulating layer over said electrode; and
    creating voids in said upper insulating layer over a portion of said electrode.

26. The method according to claim 21, wherein said step of micromachining comprises plating.

27. The method according to claim 21, wherein said step of micromachining comprises etching.

28. The method according to claim 21, wherein said step of micromachining comprises sputtering.

29. The method according to claim 21, wherein said step of micromachining comprises ion-beam assisted deposition.

30. The method according to claim 21, wherein said step of micromachining comprises photolithographic techniques.

31. The method according to claim 21, wherein said step of micromachining comprises lift-off techniques.

32. The method according to claim 21, wherein said upper conductive layer further covers portions of said base surface.

33. The method according to claim 21, wherein said upper conductive layer is formed of a material selected from the group consisting of platinum, iridium, rhodium and palladium.

34. An electrode suitable to stimulate neural tissue comprising:

a conductive electrode base defining a base surface area;

a plurality of conductive micromachined structures on the conductive electrode base, each conductive micromachined structure having a structure height and a structure width, each conductive micromachined structure covered by a conductive material, wherein said conductive layer provides enhanced stability to the electrode under electrical stimulation;

the plurality of conductive micromachined structures defining an electrode physical surface the electrode physical surface comprising surfaces of the micromachined structures in combination with portions of the base area, said surfaces of the conductive micromachined structures having an extension variable in accordance with said structure height and said structure width, wherein the structure height of each conductive micromachined structure is in the range from the structure width of said each structure to a height where combinations of the structure heights and structure widths of the plurality of micromachined structures is such that said electrode physical surface is at least four times said base surface area; and wherein said physical surface area results in at least two orders of magnitude reduction in the electrode impedance at low frequencies relative to said base surface area.

35. The electrode of claim 34, wherein said conductive micromachined structures are hermetically covered by said conductive material.

36. The electrode of claim 34, wherein said conductive material is selected from the group consisting of platinum, iridium, rhodium and palladium.

* * * * *

UNITED STATES PATENT AND TRADEMARK OFFICE
CERTIFICATE OF CORRECTION

PATENT NO. : 7,676,274 B2  Page 1 of 1
APPLICATION NO. : 10/160468
DATED : March 9, 2010
INVENTOR(S) : Andy Hung et al.

It is certified that error appears in the above-identified patent and that said Letters Patent is hereby corrected as shown below:

On the Title Page,

Item (74) Attorney, Agent, or Firm - insert --Sumana Prabhu--

Signed and Sealed this

Twenty-eighth Day of September, 2010

David J. Kappos
*Director of the United States Patent and Trademark Office*